United States Patent [19]

Morman

[11] Patent Number: 4,981,747
[45] Date of Patent: Jan. 1, 1991

[54] COMPOSITE ELASTIC MATERIAL INCLUDING A REVERSIBLY NECKED MATERIAL

[75] Inventor: Michael T. Morman, Alpharetta, Ga.

[73] Assignee: Kimberly-Clark Corporation, Neenah, Wis.

[21] Appl. No.: 248,833

[22] Filed: Sep. 23, 1988

[51] Int. Cl.$^5$ .............................................. B32B 27/14
[52] U.S. Cl. ..................................... 428/198; 156/184; 156/228; 156/229; 156/290; 428/283; 428/284; 428/287; 428/296; 428/326; 428/903
[58] Field of Search ................ 428/198, 284, 283, 287, 428/296, 326, 903, 152; 156/169, 172, 184, 228, 229, 290

[56] References Cited

U.S. PATENT DOCUMENTS

| | | | |
|---|---|---|---|
| 1,741,530 | 12/1929 | Mayer . | |
| 2,004,110 | 6/1935 | Head | 154/40 |
| 2,574,200 | 11/1951 | Teague | 23/74 |
| 2,971,322 | 2/1961 | Bouvet | 57/140 |
| 3,047,444 | 7/1962 | Harwood | 154/46 |
| 3,059,313 | 10/1962 | Harmon | 28/80 |
| 3,256,258 | 6/1966 | Herrman | 260/93.7 |
| 3,341,394 | 9/1967 | Kinney | 161/72 |
| 3,396,071 | 8/1968 | Couzens | 161/150 |
| 3,406,033 | 10/1968 | Reitz | 117/7 |
| 3,410,748 | 11/1968 | Blue | 161/76 |
| 3,438,844 | 4/1969 | Kumin | 161/150 |
| 3,485,695 | 12/1969 | Ness | 156/229 |
| 3,575,784 | 4/1971 | Phillips et al. | 161/150 |
| 3,772,417 | 11/1973 | Vogt | 264/230 |
| 3,932,682 | 1/1976 | Loft et al. | 428/296 |
| 3,949,128 | 4/1976 | Ostermeier | 428/152 |
| 4,013,816 | 3/1977 | Sabee et al. | 428/288 |
| 4,193,899 | 3/1980 | Brenner et al. | 260/23.54 |
| 4,209,563 | 6/1980 | Sisson | 428/288 |
| 4,342,812 | 8/1982 | Selwood | 428/286 |
| 4,443,513 | 4/1984 | Meitner et al. | 422/195 |
| 4,467,595 | 8/1984 | Kramers | 57/225 |
| 4,486,485 | 12/1984 | Sookne | 428/198 |
| 4,489,543 | 12/1984 | Bromley et al. | 57/208 |
| 4,515,854 | 5/1985 | Kogame et al. | 428/288 |
| 4,551,378 | 11/1985 | Carey, Jr. | 428/198 |
| 4,554,121 | 11/1985 | Kramers | 264/103 |
| 4,554,207 | 11/1985 | Lee | 428/288 |
| 4,578,307 | 3/1986 | Niki et al. | 428/288 |
| 4,606,964 | 8/1986 | Wideman | 428/152 |
| 4,612,148 | 9/1986 | Motooka et al. | 264/49 |
| 4,652,487 | 3/1987 | Mormon | 428/138 |
| 4,657,802 | 4/1987 | Mormon | 428/152 |
| 4,668,566 | 5/1987 | Braun | 428/286 |
| 4,677,695 | 7/1987 | Van Grompel et al. | 2/79 |
| 4,692,368 | 9/1987 | Taylor et al. | 428/137 |
| 4,696,779 | 9/1987 | Wideman | 264/211.13 |
| 4,720,415 | 1/1988 | Vander Wielen | 428/152 |
| 4,753,839 | 6/1988 | Greenway | 428/152 |
| 4,908,263 | 3/1990 | Reed et al. | 428/903 |
| 4,929,492 | 5/1990 | Carey et al. | 428/903 |

FOREIGN PATENT DOCUMENTS

| | | |
|---|---|---|
| 0019295 | 11/1980 | European Pat. Off. . |
| 0030418 | 6/1981 | European Pat. Off. . |
| 0127483 | 12/1984 | European Pat. Off. . |
| 0184932 | 12/1985 | European Pat. Off. . |
| 0180703 | 5/1986 | European Pat. Off. . |
| 0236091 | 2/1987 | European Pat. Off. . |
| 0237642 | 9/1987 | European Pat. Off. . |
| 1460514 | 2/1969 | Fed. Rep. of Germany . |
| 2046593 | 11/1971 | Fed. Rep. of Germany . |

(List continued on next page.)

*Primary Examiner*—James J. Bell
*Attorney, Agent, or Firm*—Karl V. Sidor

[57] ABSTRACT

A composite elastic material including at least one reversibly necked material and at least one elastic sheet joined at least at two locations in which the reversibly necked material is formed from a neckable material which has been treated so that, upon application of a force to extend the necked material to its pre-necked dimensions, the material returns generally to its necked dimensions upon termination of the force. Also disclosed is a process for making a composite elastic material by joining a reversibly necked material to an elastic sheet at least at two locations.

42 Claims, 8 Drawing Sheets

FOREIGN PATENT DOCUMENTS

| | | |
|---|---|---|
| 2613963 | 10/1977 | Fed. Rep. of Germany . |
| 2632875 | 11/1977 | Fed. Rep. of Germany . |
| 2757526 | 6/1979 | Fed. Rep. of Germany . |
| 3438859 | 7/1985 | Fed. Rep. of Germany . |
| 2205407 | 5/1974 | France . |
| 648644 | 1/1951 | United Kingdom . |
| 1217498 | 12/1970 | United Kingdom . |
| 1308904 | 3/1973 | United Kingdom . |
| 1399666 | 7/1975 | United Kingdom . |
| 1487488 | 9/1977 | United Kingdom . |
| 1532467 | 11/1978 | United Kingdom . |
| 1538671 | 1/1979 | United Kingdom . |
| 1575972 | 10/1980 | United Kingdom . |
| 1576436 | 10/1980 | United Kingdom . |
| 2149720 | 6/1985 | United Kingdom . |
| 2175026 | 11/1986 | United Kingdom . |

A > B

COMPOSITE ELASTIC MATERIAL INCLUDING A REVERSIBLY NECKED MATERIAL

FIELD OF THE INVENTION

The present invention relates to the field of elasticized materials and a method of making the same. Generally speaking, the present invention relates to composite elastic laminates.

BACKGROUND OF THE INVENTION

Plastic nonwoven webs formed by nonwoven extrusion processes such as, for example, meltblowing processes and spunbonding processes may be manufactured into products and components of products so inexpensively that the products could be viewed as disposable after only one or a few uses. Representatives of such products include diapers, tissues, pads, wipes, garments and feminine care products.

Some of the problems in this area are the provision of an elastic material which is resilient and flexible while still having a pleasing feel. One problem is to provide an elastic material which does not feel plastic or rubbery. The properties of the elastic materials can be improved by forming a composite of an elastic material with one or more nonelastic materials on the outer surface which provide better tactile properties.

Nonwoven webs formed from nonelastic polymers such as, for example, polypropylene, are generally considered nonelastic. The lack of elasticity usually restricts these nonwoven web materials to applications where elasticity is not required or desirable.

Composites of elastic and nonelastic material have been made by bonding the nonelastic material to the elastic material in a manner that allows the entire composite to stretch or elongate so they may be used in garment materials, pads, diapers and feminine care products.

In one such composite material, a nonelastic material is bonded to an elastic material while the elastic material is in a stretched condition so that when the elastic material is relaxed, the nonelastic material gathers between the locations where it is bonded to the elastic material. The resulting composite elastic material is stretchable to the extent that the nonelastic material gathered between the bond locations allows the elastic material to elongate. An example of this type of composite material is disclosed, for example, by U.S. Pat. No. 4,720,415 to Vander Wielen et al., issued Jan. 19, 1988.

DEFINITIONS

The term "elastic" is used herein to mean any material which, upon application of a biasing force, is stretchable, that is, elongatable, to a stretched, biased length which is at least about 160 percent of its relaxed unbiased length, and which, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be stretched by much more than 60 percent of their relaxed length, for example, 100 percent or more, and many of these will recover to substantially their original relaxed length, for example, to within 105 percent of their original relaxed length, upon release of the stretching force.

As used herein, the term "nonelastic" refers to any material which does not fall within the definition of "elastic," above.

As used herein, the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length final sample length)/(maximum stretch length - initial sample length)] $\times$ 100.

As used herein, the term "nonwoven web" means a web having a structure of individual fibers or threads which are interlaid, but not in an identifiable, repeating manner. Nonwoven webs have been, in the past, formed by a variety of processes such as, for example, meltblowing processes, spunbonding processes and bonded carded web processes.

As used herein, the term "microfibers" means small diameter fibers having an average diameter not greater than about 100 microns, for example, having a diameter of from about 0.5 microns to about 50 microns, or more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spun-bonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

As used herein, the term "sheet" means a layer which may either be a film or a nonwoven web.

As used herein, the term "necked material" refers to any material which has been constricted in at least one dimension by processes such as, for example, drawing or gathering.

As used herein, the term "neckable material" means any material which can be necked.

As used herein, the term "reversibly necked material" refers to a material formed from a material that has been treated while necked to impart memory to the material so that, when a force is applied to extend the material to its pre-necked dimensions, the treated, necked portions will generally recover to their necked dimensions upon termination of the force. One form of treatment is the application of heat. Generally speaking, extension of the reversibly necked material is limited to extension to its pre-necked dimensions. Therefore, unless the material is elastic, extension too far beyond its pre-necked dimensions will result in material failure. A reversibly necked material may include more than one layer. For example, multiple layers of spunbonded web, multiple layers of meltblown web, multiple layers of bonded carded web or any other suitable material or mixtures thereof.

As used herein, the term "percent neckdown" refers to the ratio determined by measuring the difference between the unconstricted dimension and the constricted dimension of a neckable material and then dividing that difference by the unconstricted dimension of the-neckable material.

As used herein, the term "composite elastic material" refers to a material having at least two layers with at least one of the layers being an elastic sheet and at least one of the layers being a reversibly necked material. The elastic sheet may be joined to the reversibly necked stretchable material at intermittent points or areas or may be substantially joined thereto over the entire area of juxtaposition. The joining is accomplished while the elastic sheet and the reversibly necked material are in juxtaposed configuration. The composite elastic material is elastic in a direction generally parallel to the direction of neckdown of the reversibly necked material and may be stretched in that direction to the breaking point of one of the components of the laminate. The composite elastic material may include more than two layers. For example, the elastic sheet may have a reversibly necked material joined to both of its sides so that a three-layer composite elastic material is formed having a structure of reversibly necked material/elastic sheet/reversibly necked material. Additional elastic sheets and/or reversibly necked material layers may be added. Yet other combinations of elastic sheets and reversibly necked materials may be used.

As used herein, the term "palindromic laminate" means a multilayer laminate, for example, a composite elastic material which is substantially symmetrical. Exemplary palindromic laminates would have layer configurations of A/B/A, A/B/B/A, A/A/B/B/A/A, etc. Exemplary non-palindromic laminates would have layer configurations of A/B/C, A/B/C/A, A/C/B/D, etc.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

SUMMARY OF THE INVENTION

The present invention provides a method of producing a composite elastic material including one or more layers of reversibly necked material joined to one or more layers of elastic sheet at least at two locations.

The elastic sheet and the reversibly necked material may be joined by overlaying the materials and applying heat and/or pressure to the overlaid materials. Alternatively, the layers may by joined by using other bonding methods and materials such as, for example, adhesives, pressure sensitive adhesives, ultrasonic welding, high energy electron beams, and/or lasers. In one aspect of the present invention, the elastic sheet may be formed directly on the reversibly necked material utilizing processes, such as, for example, meltblowinq processes and film extrusion processes.

The reversibly necked material used as a component of the composite elastic material is formed from a neckable material. If the material is stretchable, it may be necked by stretching in a direction generally perpendicular to the desired direction of neck-down. Alternatively, the material may be compacted to effect neckdown. Memory may be imparted to certain necked materials so that, when a force is applied to extend the necked materials to their pre-necked dimensions, the materials return generally to their necked dimensions upon termination of the force. Such memory may be imparted to necked materials by:

heating the necked materials; and
cooling the materials while they are still in the necked configuration.

According to the present invention, the reversibly necked material may be made from any neckable material that can be treated to acquire such memory characteristics. Such neckable materials include, for example, bonded carded webs, spunbonded webs or meltblown webs. The meltblown web may include meltblown microfibers. The reversibly necked material may also include multiple layers such as, for example, multiple spunbond layers and/or multiple meltblown layers. The reversibly necked material may be made of polymers such as, for example, polyolefins. For example, the polyolefins may be thermoplastic polyolefins such as polyethylene, polypropylene, polybutene, ethylene copolymers, propylene copolymers, butene copolymers and combinations of the above.

The elastic sheet may be a pressure sensitive elastomer adhesive sheet. If the elastic sheet is nonwoven web of elastic fibers or pressure sensitive elastomer adhesive fibers, the fibers may be meltblown fibers. The meltblown fibers may include meltblown microfibers.

Other aspects of this invention provide that the pressure sensitive elastomer adhesive sheet and reversibly necked material may be joined without the application of heat such as, for example, by pressure nip roll arrangements or by tensioned wind-up techniques.

DETAILED DESCRIPTION OF THE INVENTION

Figure 1:
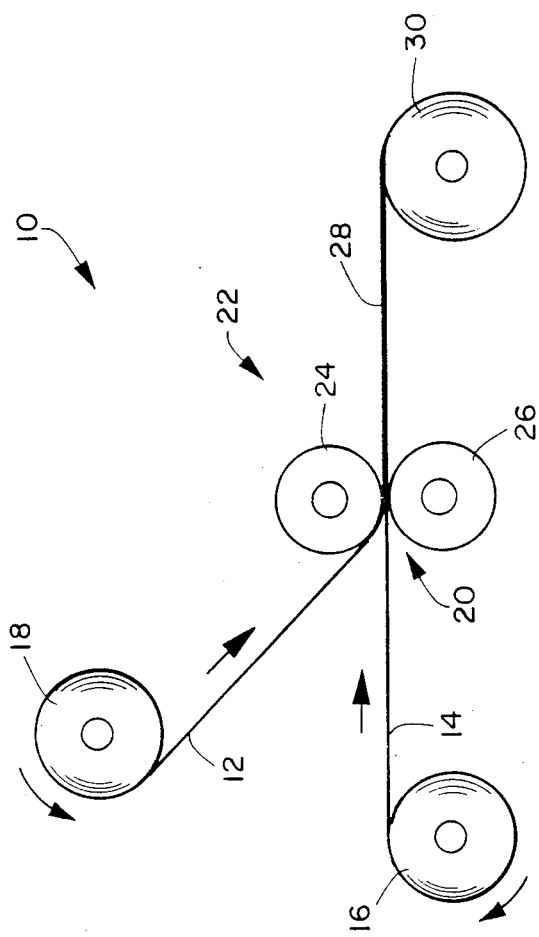
FIG. 1 is a schematic representation of an exemplary process for forming a composite elastic material.

Referring to the drawings where like reference numerals represents like materials or process steps and, in part, to FIG. 1 there is schematically illustrated at 10 a process for forming a composite elastic material by joining an elastic sheet 12 to a reversibly necked material 14.

According to the present invention, the reversibly necked material 14 is unwound from a supply roll 16 of the material 14 and travels in the direction indicated by the arrow associated therewith as the supply roll 16 rotates in the direction of the arrows associated therewith.

An elastic sheet 12 is unwound from a supply roll 18 and travels in the direction indicated by the arrow associated therewith as the supply roll 18 rotates in the direction of the arrows associated therewith. The elastic sheet 12 may be formed by extrusion processes such as, for example, meltblowing processes or film extrusion processes and used in the method of the present invention without first being stored on a supply roll.

The reversibly necked material 14 passes through a pressure nip 20 formed by the bonder roller arrangement 22. Since the reversibly necked material 14 maintains its necked dimensions even without a necking force, there is no need to maintain tension upon the reversibly necked material 14 in order to keep it in a necked condition. The only tension required is tension to maintain control of the material. The elastic sheet 12 also passes through the pressure nip 20 formed by the rollers 24 and 26 of the bonder roller arrangement 22. The reversibly necked elastic material 14 and the elastic sheet 12 are joined during their passage through the bonder roller arrangement 22 to form a composite elastic material 28 which is wound on wind-up roll 30.

The elastic sheet 12 may be a multilayer material in that it may include two or more individual coherent webs or films. Additionally, the elastic sheet 12 may be a multilayer material in which one or more of the layers contain a mixture of elastic and nonelastic fibers and/or particulates. An example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such a composite web would be one made by a technique such as disclosed in U.S. Pat. No. 4,100,324 issued July 11, 1978 to Richard A. Anderson et al., and also incorporated herein by reference. That patent discloses a nonwoven material which includes a mixture of meltblown thermoplastic fibers and other materials which are combined in the gas stream in which the meltblown fibers are borne so that an intimate entangled commingling of meltblown thermoplastic fibers and other materials, e.g., wood pulp, staple fibers or particulates such as, for example, hydrocolloid (hydrogel) particulates commonly referred to as superabsorbents occurs prior to collection of the fibers upon a collecting device to form a coherent web of randomly dispersed fibers.

The elastic sheet 12 maY be made from any material which may be manufactured in sheet form. Generally, any suitable elastomeric fiber forming resins or blends containing the same may be utilized for the nonwoven webs of elastomeric fibers of the invention and any suitable elastomeric film forming resins or blends containing the same may be utilized for the elastomeric films of the invention.

For example, the elastic sheet 12 may be made from block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The elastic sheet 12 may be formed from, for example, (polystyrene/poly(ethylene-butylene)/polystyrene) block copolymers available from the Shell Chemical Company under the trademark KRATON G. One such block copolymer may be, for example, KRATON G-1657.

Other exemplary elastomeric materials which may be used to form elastic sheet 12 include polyurethane elastomeric materials such as, for example, those available under the trademark ESTANE from B. F. Goodrich & Co., polyamide elastomeric materials such as, for example, those available under the trademark PEBAX from the Rilsan Company, and polyester elastomeric materials such as, for example, those available under the trade designation Hytrel from E. I. DuPont De Nemours & Company. Formation of elastic sheets from polyester elastic materials is disclosed in, for example, U.S. Pat. No. 4,741,949 to Morman et al., hereby incorporated by reference.

A polyolefin may also be blended with the elastomeric polymer to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothaene NA601 (also referred to herein as PE NA601 or polyethylene NA601). Two or more of the polyolefins may be utilized. Extrudable blends of elastomeric polymers and polyolefins are disclosed in, for example, U.S. Pat. No. 4,663,220 to Wisneski et al., hereby incorporated by reference.

The elastic sheet 12 may be a pressure sensitive elastomer adhesive sheet. For example, the elastic material itself may be tacky or, alternatively, a compatible tackifying resin may be added to the extrudable elastomeric compositions described above to provide an elastomeric sheet that can act as a pressure sensitive adhesive, e.g., to bond the elastomeric sheet to a reversibly necked material. In regard to the tackifying resins and tackified extrudable elastomeric compositions, note the resins and compositions as described in U.S. Pat. No. 4,789,699 of J. S. Keiffer and T. J. Wisneski for "Ambient Temperature Bondable Elastomeric Nonwoven Web", hereby incorporated by reference.

Any tackifier resin can be used which is compatible with the elastomeric polymer and can withstand the high processing (e.g., extrusion) temperatures. If blending materials such as, for example, polyolefins or extending oils are used, the tackifier resin should also be compatible with those blending materials. Generally, hydrogenated hydrocarbon resins are useful tackifying resins, because of their better temperature stability. REGALREZ TM and ARKON TM P series tackifiers are examples of hydrogenated hydrocarbon resins. ZONATAK TM 501 lite is an example of a terpene hydrocarbon. REGALREZ hydrocarbon resins are available from Hercules Incorporated. ARKON P series resins are available from Arakawa Chemical (U.S.A.) Incorporated. Of course, the present invention is not limited to use of such three tackifying resins, and other tackifying resins which are compatible with the composition and can withstand the high processing temperatures, can also be used.

A pressure sensitive elastomer adhesive may include, for example, from about 40 to about 80 percent by weight elastomeric polymer, from about 5 to about 40 percent polyolefin and from about 5 to about 40 percent resin tackifier. For example, a particularly useful composition included, by weight, about 61 to about 65 percent KRATON G-1657, about 17 to about 23 percent Polyethylene NA-601, and about 15 to about 20 percent REGALREZ 1126.

The bonder roller arrangement 22 may be a smooth calender roller 24 and a smooth anvil roller 26 or may include a patterned calender roller such as, for example, a pin embossing roller arranged with a smooth anvil roller. One or both of the calender roller and the smooth anvil roller may be heated and the pressure between the two rollers may be adjusted by well-known means to provide the desired temperature, if any, and bonding pressure to join the reversibly necked material 14 to the elastic sheet 12 forming the composite elastic material 28.

The reversibly necked material 14 and the elastic sheet 12 may be completely bonded together and still provide a composite elastic material 28 with good stretch properties. That is, a composite elastic material 28 may be formed by joining reversibly necked material 14 to an elastic sheet 12 utilizing smooth rollers or platens to provide a high bond surface area which approaches 100 percent. For example, one composite elastic material formed in this manner utilizing flat platens had a bond surface area which approached 100 percent and a cross-machine direction elongation of about 140 percent. A composite elastic material 28 may also be formed utilizing a bonding pattern such as, for example, the sinusoidal bonding pattern shown in FIG. 9. That pattern has approximately 75 pins per square inch with each pin about 0.059 inches in diameter, providing a bond surface area of about 20.5 percent.

Reversibly necked materials may be joined to the elastic sheet 12 at least at two places by any suitable means, such as, for example, thermal bonding or ultrasonic welding which softens at least portions of at least one of the materials, usually the elastic sheet because the elastomeric materials used for forming the elastic sheet 12 have a lower softening point than the components of the reversibly necked material 14. Joining may be produced by applying heat and/or pressure to the overlaid elastic sheet 12 and the reversibly necked material 14 by heating these portions (or the overlaid layer) to at least the softening temperature of the material with the lowest softening temperature to form a reasonably strong and permanent bond between the resolidified softened portions of the elastic sheet 12 and the reversibly necked material 14.

Elastic sheets can be used having basis weights less than 0.5 osy (ounces per square yard), for example, from about 0.25 to about 0.4 osy. Such extremely low basis weight sheets are useful for economic reasons, particularly for use in disposable products. Additionally, elastic sheets having higher basis weights such as, for example, from about 0.5 to about 10.0 osy may also be used.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. However, for a given combination of materials, and in view of the herein contained disclosure the processing conditions necessary to achieve satisfactory bonding can be readily determined by one of skill in the art.

Conventional drive means and other conventional devices which may be utilized in conjunction with the apparatus of FIG. 1 are well known and, for purposes of clarity, have not been illustrated in the schematic view of FIG. 1.

The relation between the width of the reversibly necked material 14 to its width before constriction and heat treatment determines the approximate limits of extension of the composite elastic material 28. Generally speaking, extension of the reversibly necked material is limited to extension to about its pre-necked dimensions. Extension too far beyond its pre-necked dimensions will result in material failure. Therefore, the composite elastic material 28 can be extended to generally the same limits as the reversibly necked material 14.

Figure 2:
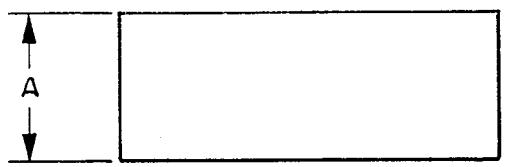
FIG. 2 is a plan view of an exemplary neckable material before tensioning and necking.
Figure 2A:
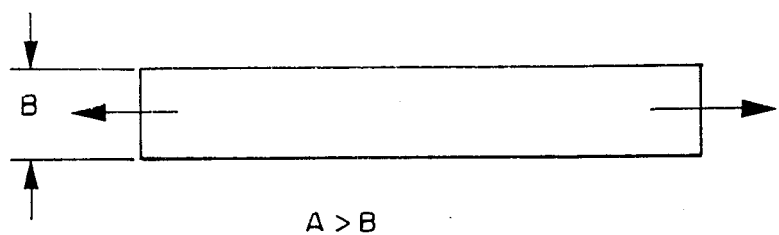
FIG. 2A is a plan view of an exemplary reversibly necked material.
Figure 2B:
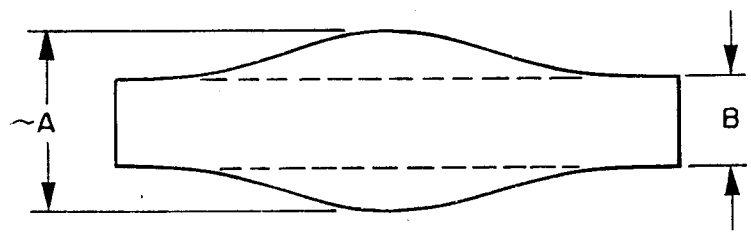
FIG. 2B is a plan view of an exemplary composite elastic material including a reversibly necked material while partially stretched.

For example, with reference to FIGS. 2, 2A, and 2B, if it is desired to prepare a composite elastic material including a reversibly necked material which is stretchable to a 150% elongation, a neckable material shown schematically and not necessarily to scale in FIG. 2 having a width "A" such as, for example, 250 cm, is necked to a width "B" of about 100 cm and is heat treated while necked to impart a memory of its necked configuration shown in FIG. 2A. The resulting reversibly necked material is then joined in the necked configuration to an elastic sheet having a width of approximately 100 cm and which is extendable at least to a width of about 250 cm. The composite elastic material produced in this manner and shown schematically and not necessarily to scale in FIG. 2B has a width "B" of about 100 cm may be stretched to at least the original 250 cm width "A" of the reversibly necked material for an elongation of about 150%. As can be seen from the example, the elastic limit of the elastic sheet needs only to be as great as the minimum desired elastic limit of the composite elastic material.

Figure 3:
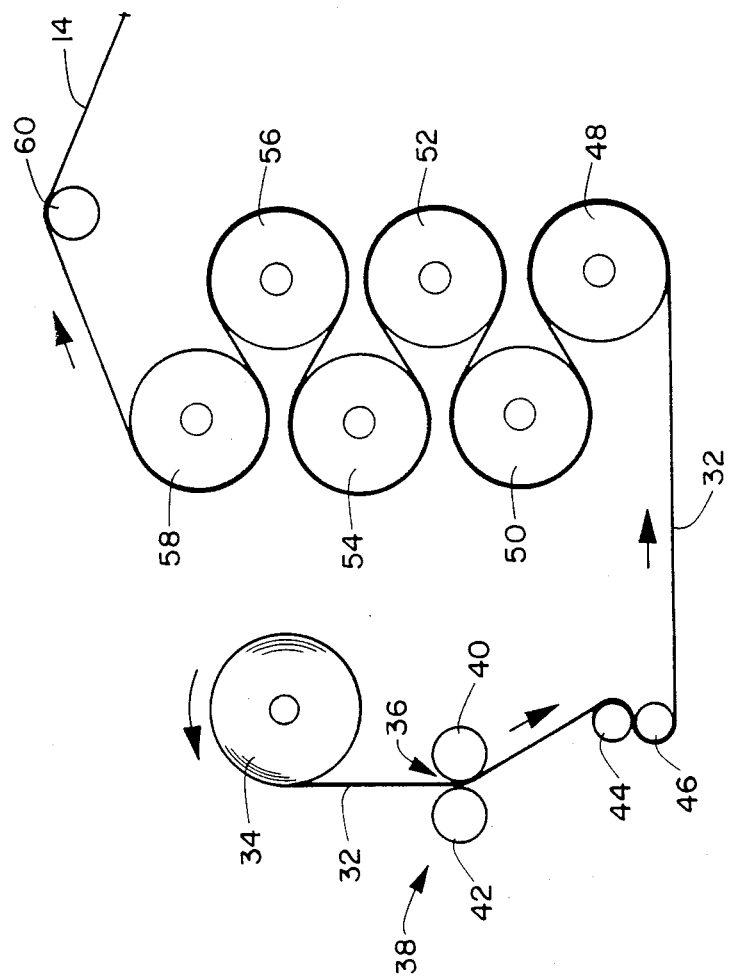
FIG. 3 is a schematic representation of an exemplary process for forming a reversibly necked material component of a composite elastic material.

FIG. 3 illustrates an exemplary process of making the reversibly necked material component 14 of a composite elastic material 28. A neckable material 32 is unwound from a supply roll 34 and travels in the direction indicated by the arrow associated therewith as the supply roll 34 rotates in the direction of the arrows associated therewith. The neckable material 32 passes through the nip 36 of a drive roller arrangement 38 formed by the drive rollers 40 and 42 and then past the idler rolls 44 and 46.

The neckable material 32 may be formed by known nonwoven extrusion processes, such as, for example, known meltblowing processes or known spunbonding processes, and passed directly through the nip 36 without first being stored on a supply roll.

After passing through the nip 36 of the driver roller arrangement 38 and the idler rollers 44 and 46, the neckable material 32 passes over a series of steam cans 48-58 in a series of reverse S loops as indicated by the rotation direction arrows associated with the steam cans. The steam cans 48-58 typically have an outside diameter of about 24 inches although other sized cans may be used. The contact time or residence time of the neckable material on the steam cans to effect heat treatment will vary depending on factors such as, for example, steam can temperature, type of material and the basis weight of the material. For example, a necked web of polypropylene may be passed over a series of steam cans heated to a measured temperature from about 90° to about 150° C. (194°-302° F.) for a contact time of 5 to about 300 seconds to effect heat treatment. More particularly, the temperature may range from about 125° to about 143° C. and the residence time may range from about 2 to about 50 seconds.

Because the peripheral linear speed of the drive rollers 40 and 42 of the drive roller arrangement 38 is controlled to be lower than the peripheral linear speed of the steam cans 48-58, the neckable material 32 is tensioned between the steam cans 48-58 and the nip 36 of the drive roller arrangement 38. By adjusting the difference in the speeds of the rollers, the neckable material 32 is tensioned so that it necks a desired amount and is maintained in the necked condition while passing over the heated steam cans 48-58. This action imparts memory to the neckable material 32 of its necked condition. The neckable material 32 is then cooled in the necked condition as it passes the idler roller 60 to form the reversibly necked material 14. That is, a material which is adapted to stretch to at least its original, pre-necked dimensions upon application of a stretching force in a direction generally parallel to the direction of necking and then recover to about its reversibly necked dimensions upon release of the stretching force.

The neckable material 32 may be a nonwoven material such as, for example, spunbonded web, meltblown web or bonded carded web. If the neckable material 32 is a web of meltblown fibers, it may include meltblown microfibers. The neckable material 32 is made from any material that can be treated while necked so that, upon application of a force to extend the necked material to its pre-necked dimensions, the material returns generally to its necked dimensions upon termination of the force. Certain polymers such as, for example, polyolefins, polyesters and polyamides may be heat treated by, for example, heat, under suitable conditions to impart such memory. Exemplary polyolefins include one or more of polyethylene, polypropylene, polybutene, ethylene copolymers, propylene copolymers, and butene copolymers. Polypropylenes that have been found useful include, for example, polypropylene available from the Himont Corporation under the trade designation PC-973, polypropylene available from the Exxon Chemical Company under the trade designation Exxon 3445, and polypropylene available from the Shell Chemical Company under the trade designation DX 5A09.

In one embodiment of the present invention, the neckable material 32 is a multilayer material having, for example, at least one layer of spunbonded web joined to at least one layer of meltblown web, bonded carded web or other suitable material. For example, neckable material 32 may be a multilayer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the neckable material 32 may be single layer of material such as, for example, a spunbonded web having a basis weight of from about 0.2 to about 10 osy or a meltblown web having a basis weight of from about 0.2 to about 8.0 osy.

The neckable material 32 may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as super-absorbents occurs prior to collection of the meltblown fibers upon a collecting device to form a coherent web of randomly dispersed meltblown fibers and other materials such as disclosed in previously referenced U.S. Pat. No. 4,100,324.

If the neckable material 32 is a nonwoven web of fibers, the fibers should be joined by interfiber bonding to form a coherent web structure which is able to withstand necking. Interfiber bonding may be produced by entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding.

Although the present invention should not be held to a particular theory of operation, the heat treatment should raise the neckable material 32 to a temperature range for a specified time period where it is believed that additional polymer crystallization occurs while the material is in the necked condition. Because certain types of fibers are formed by methods such as, for example, meltblowing and spunbonding which cool the fibers very quickly, it is believed that the polymers forming the fibers are not fully crystallized. That is, the polymers harden before the crystallization is complete. It is believed that additional crystallization can be effected by increasing the temperature of the material to a temperature below the material's melting point. When this additional crystallization occurs while the material is in the necked condition, it is believed that memory of the necked condition is imparted to the material.

Figure 4A:
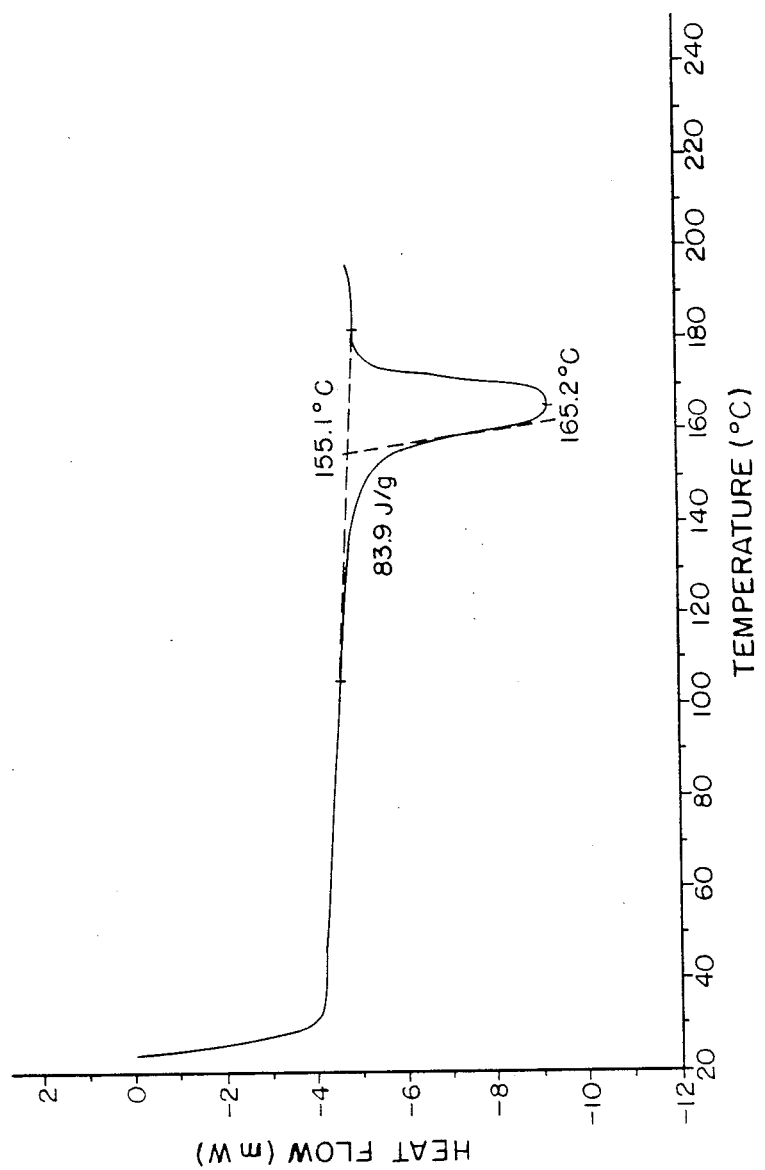
FIG. 4A is an exemplary Differential Scanning Calorimetry scan of a neckable material before heat treatment.
Figure 4B:
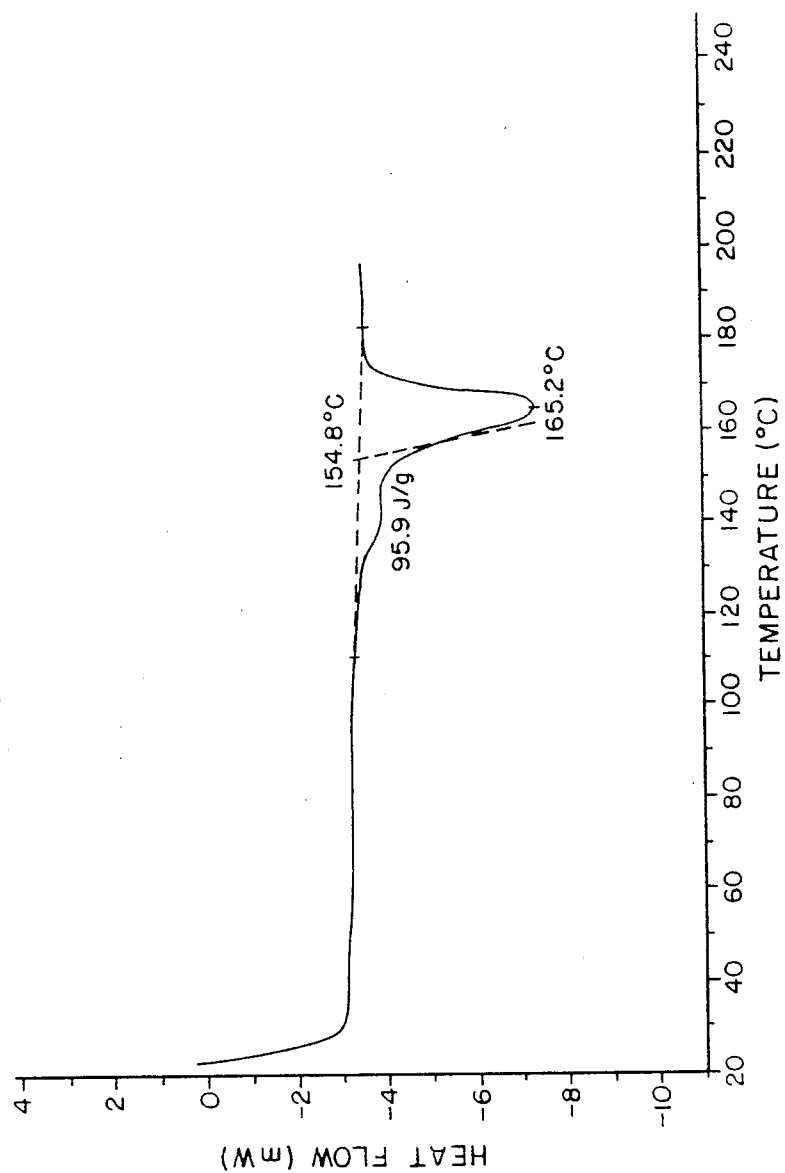
FIG. 4B is an exemplary Differential Scanning Calorimetry scan of a reversibly necked material, i.e., after treatment while necked.

FIG. 4A is an exemplary Differential Scanning Calorimetry scan of a spunbonded polypropylene material by a Model 1090 Thermal Analyzer available from Du Pont Instruments. FIG. 4B is an exemplary Differential Scanning Calorimetry scan of the same type of spunbonded polypropylene material which has been necked and heat treated. Differential Scanning Calorimetry can be used to show that neckable materials such as, for example, spunbonded webs, which have been necked and heat treated exhibit greater heats of fusion than the same materials which have not been heat treated. That is, the heat of fusion of a reversibly necked material is typically at least about 5 percent greater than the material before being reversibly necked. For example, from about 5 to about 15 percent greater. Additionally, the onset of melting occurs at lower temperatures for necked and heat treated materials than for their non-heat treated counterparts. That is, the onset of melting of a reversibly necked material typically occurs at a temperature at least about 5° C. lower than for the material before being reversibly necked. For example, at a temperature from about 5° to about 15° C. lower. A greater heat of fusion is believed to result from additional crystallization which occurs during heat treatment. A lower temperature for onset of melting is believed to result from imperfect or strained crystals formed during heat treatment of the material while in the necked condition.

Figure 5:
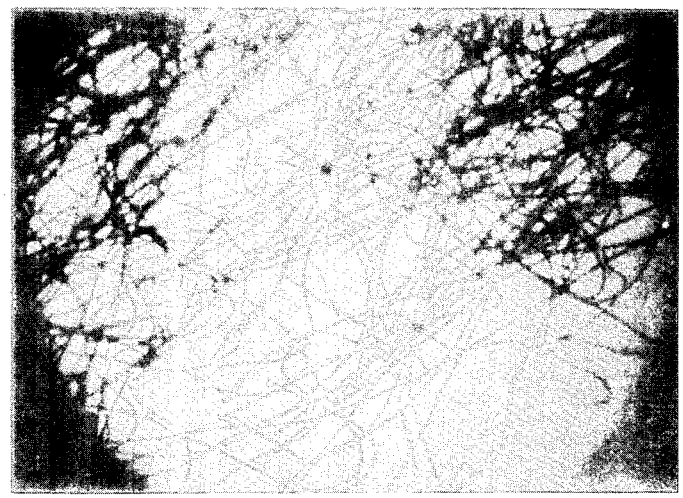
FIG. 5 is an enlarged photomicrograph of an exemplary reversibly necked material used as a component of a composite elastic material.
Figure 6:
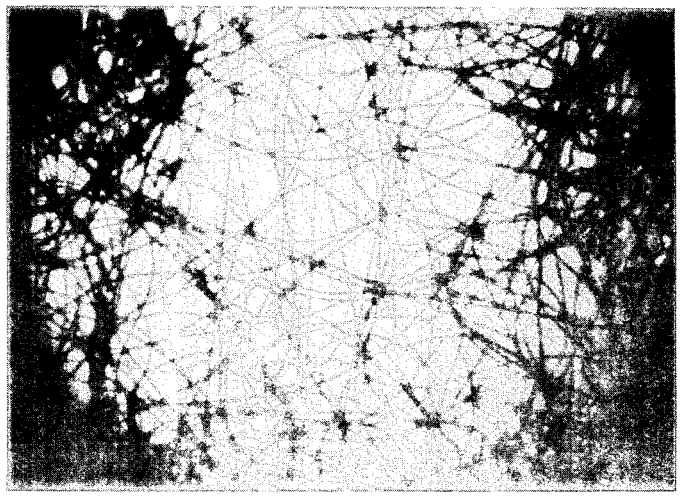
FIG. 6 is an enlarged photomicrograph of an exemplary neckable material, prior to treatment while necked.

Tensioning and heat treatment of nonelastic material 32 also adds crimps and kinks to the material as shown in FIG. 5, particularly when compared to the untreated material shown in FIG. 6. These crimps and kinks are believed to add to the stretch and recovery properties of the material.

Figure 7:
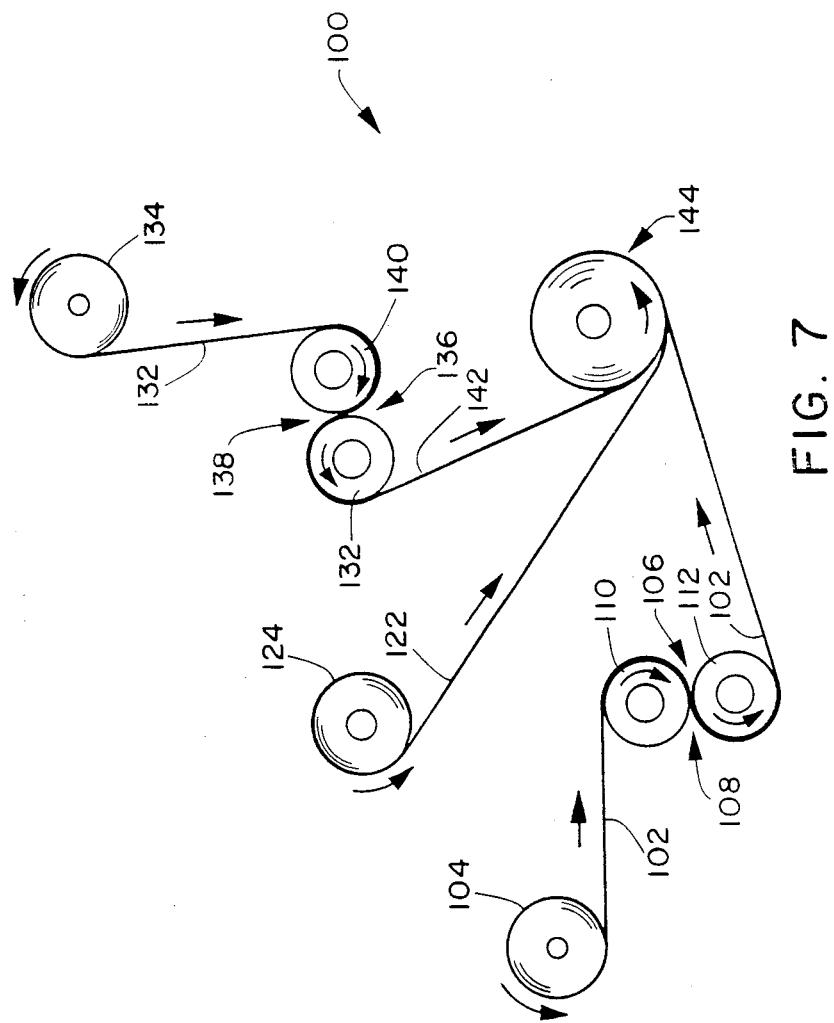
FIG. 7 is a schematic representation of an exemplary process for forming a composite elastic material using a tensioned wind-up method.

Referring now to FIG. 7 of the drawings, there is schematically illustrated at 100 a process for forming a composite elastic material by a tensioned wind-up method. A first reversibly necked material 102 is unwound from a supply roll 104 and a second reversibly necked material 132 is unwound from a supply roll 134. The reversibly necked materials 102 and 132 then travel in the direction indicated by the arrows associated therewith as the supply rolls 104 and 134 rotate in the direction of the arrow associated therewith. The reversibly necked material 102 passes through the nip 106 of the S-roll arrangement 108 formed by the stack rollers 110 and 112. Likewise, the reversibly necked material 132 passes through the nip 136 of the S-roll arrangement 138 formed by the stack rollers 140 and 142. Alternatively, the reversibly necked materials 102 and 132 may be formed by known nonwoven extrusion processes such as, for example, spunbonding or meltblowing processes, and necked and heat treated utilizing, for example, a series of steam cans and then passed through the nips 106 and 136 without first being stored on supply rolls.

An elastic sheet 122 is unwound from a supply roll 124 and travels in the direction indicated by the arrow associated therewith as the supply roll 124 rotates in the direction of the arrows associated therewith. The elastic sheet 122 may be formed by known extrusion processes such as, for example, known meltblowing processes or known film extrusion processes without first being stored on a supply roll. The elastic sheet 122 may be a pressure sensitive elastomer adhesive sheet such as, for example, an elastic sheet formed from a composition including an elastic polymer and a tackifying resin.

The reversibly necked material 102 then passes through the nip 106 of the S-roll arrangement 108 in a reverse-S wrap path as indicated by the rotation direction of the arrows associated with stack rollers 110 and 112. Likewise, the reversibly necked material 132 passes through the nip 136 of the S roll arrangement 138 in a reverse-S wrap path as indicated by the rotation direction arrows associated with the stack rollers 140 and 142. Because the peripheral linear speeds of the rollers of the S-roller arrangements 108 and 138 are controlled to be less than the peripheral linear speed of the rollers of the wind-up roll 144, the reversibly necked materials 102 and 132 are tensioned so that they sandwich the elastic sheet 122 as they are wound up on the wind-up roll 144. Tension from the reversibly necked materials 102 and 132 activate the pressure sensitive elastic sheet 122 so that the layers join forming a composite elastic material on wind-up roll 144.

The wind-up roll 144 of reversibly necked material/elastic sheet layers may also be heated in an oven (not shown) to soften the elastic sheet to facilitate bonding between the elastic sheet and the reversibly necked materials to form a composite elastic material.

A two layer composite in which one side of the of the elastic sheet is protected to prevent bonding (e.g., covered with a plastic film) may be formed by the above-described method. Multilayer materials having multiple layers of elastic sheet and multiple layers of reversibly necked material such as, for example, palindromic laminates, may also be formed by the same method.

The above-described tensioned wind-up bonding methods are suited for low basis weight elastic sheets because bonding takes place in the absence of tension on the elastic sheet. As to the bonding pressure utilized when bonding is effected by the above-described tensioned wind-up method, specification of a bonding pressure does not, in itself, take into account complicating factors such as, for example, the basis weight of the materials or the bonding compatibility of elastic sheet and the reversibly necked materials. Nonetheless, one skilled in the art, taking into account such factors will readily be able to appropriately select and vary an effective bonding pressure.

Conventional drive means and other conventional devices which may be utilized in conjunction with the apparatus of FIG. 7 are well known and, for purposes of clarity, have not been illustrated in the schematic view of FIG. 7.

Figure 8:
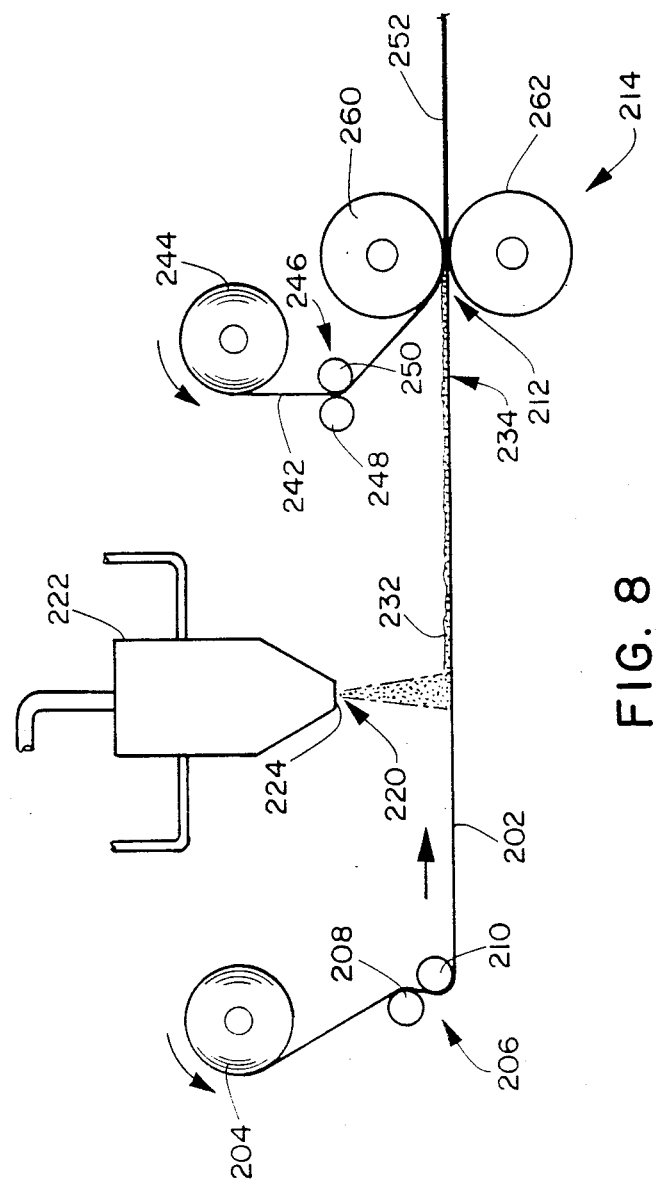
FIG. 8 is a schematic representation of an exemplary process for forming a composite elastic material by meltblowing an elastic web between two layers of reversibly necked elastic material.

Referring now to FIG. 8 of the drawings, there is schematically illustrated at 200 an exemplary process for forming a composite elastic material by meltblowing a web of elastic fibers onto a first reversibly necked material, overlaying a second reversibly necked material and then joining the layers with a bonder roller arrangement.

A first reversibly necked material 202 is unwound from a supply roll 204. The reversibly necked material 202 then travels in the direction indicated by the arrow associated therewith as the supply roll 204 rotates in the direction of the arrow associated therewith. The reversibly necked material 202 then passes through an idler roller arrangement 206 formed by the idler rollers 208 and 210. Alternatively, the reversibly necked material 202 may be formed by known nonwoven extrusion processes, such as, for example, known spunbonding or known meltblowing processes, and necked and heat treated utilizing, for example, a series of steam cans and then passed directly through the idler roller arrangement 206 without first being stored on a supply roll.

The reversibly necked material 202 passes under the meltblowing process equipment 222 as an elastic sheet 232 of elastomeric meltblown fibers 220 is formed directly on the reversibly necked material 202 thereby forming a composite elastic material 234. A stream of elastomeric meltblown fibers 220 is directed from the meltblowing process equipment 222 onto a reversibly necked material 202 at a high velocity while the fibers are in a softened state so that bonding and/or entangling occurs between the deposited elastomeric sheet 232 of meltblown fibers 220 and the reversibly necked material 202. The meltblown fibers may include meltblown microfibers.

Generally, the fibers of the meltblown fiber stream 220 bond adequately to the reversibly necked material 202 when the fibers have an initial high velocity, for example, from about 300 feet per second to about 1000 feet per second. Additionally, the vertical distance from the forming nozzle 224 of the meltblowing process equipment 222 to the reversibly necked elastic material 02 may range from about 4 to about 18 inches. More particularly, the vertical distance may be set at about 12 inches. The elastic sheet 232 may also be formed by other extrusion processes such as, for example, film extrusion processes.

A second reversibly necked material 242 is unwound from a supply roll 244. The reversibly necked material 242 then travels in the direction indicated by the arrow associated therewith as the supply roll 244 rotates in the direction of the arrow associated therewith. The reversibly necked material 242 then passes through an idler roller arrangement 246 formed by idler rollers 248 and 250. Alternatively, the reversibly necked material 242 may be formed by nonwoven extrusion processes, such as, for example, spunbonding or meltblowing processes, and necked and heat treated utilizing, for example, a series of steam cans and then passed directly through the idler roller arrangement 246 without first being stored on a supply roll.

The reversibly necked material 242 is overlaid on the elastic sheet 232 and the reversibly necked elastic material 202. The three layers are passed through a nip 212 of a bonder roller arrangement 214 to produce a composite elastic material 252. The bonder roller arrangement 214 may be a patterned calender roller 260 arranged with a smooth anvil roller 262. A smooth calender roller may also be used. One or both of the calender roller 260 and the anvil roller 262 may be heated and the pressure between these two roller may be adjusted to provide the desired temperature and bonding pressure to join the reversibly necked material layers 202 and 242 with the elastic sheet 232. Other bonding methods such as, for example, ultrasonic welding, laser beams, and high energy electron beams may also be used to bond the reversibly necked material layers 202 and 242 with the elastic sheet 232. The bond surface area on composite elastic material 252 may be as high as about 100 percent and still provide a composite elastic material with good stretch properties.

Generally, any suitable elastomeric fiber forming resins or blends containing the same may be utilized for the nonwoven webs of elastomeric fibers of the invention and any suitable elastomeric film forming resins or blends containing the same may be utilized for the elastomeric films of the invention.

The elastic sheet 232 of elastomeric meltblown fibers 220 may be formed from elastomeric polymers such as, for example, block copolymers having the general formula A—B—A' where A and A' are each a thermoplastic polymer endblock which contains a styrenic moiety such as a poly (vinyl arene) and where B is an elastomeric polymer midblock such as a conjugated diene or a lower alkene polymer. One such block copolymer may be, for example, KRATON G-1657.

Other exemplary elastomeric materials which may be used to form the elastic sheet 232 include polyester elastomeric materials such as, for example, those available under the trade designation Hytrel from E. I. DuPont De Nemours & Co., polyurethane elastomeric materials such as, for example, those available under the trademark ESTANE from B. F. Goodrich & Co., and polyamide elastomeric materials such as, for example, those available under the trademark PEBAX from the Rilsan Company.

The elastic sheet 232 may also be a pressure sensitive elastomer adhesive sheet. For example, the elastic sheet 232 may be formed from a blend of about 63% by weight KRATON G-1657, 20% polyethylene NA-601, and 17% REGALREZ 1126 having a melt flow of from about 12 grams per ten minutes to about 18 grams per ten minutes when measured at 190° C. and under a 2160 gram load; an elongation of about 750% a modulus of elongation at 100% of from about 155 to about 200 psi; and a modulus of elongation at 300% of from about 200 to about 250 psi. More particularly, the blend may have a melt flow of about 15 grams per ten minutes when measured at 190° C. and under a 2160 gram load; an elongation of about 750% a modulus of elongation at 100% of about 175 psi; and a modulus of elonqation at 300% of about 225 psi. Such materials are described, for example in previously referenced U.S. Pat. No. 4,789,699 of J. S. Keiffer and T. J. Wisneski for "Ambient Temperature Bondable Elastomeric Nonwoven Web." For example, the elastic sheet 232 may be a meltblown web of pressure sensitive elastomer adhesive fibers. In such case, joining the reversibly necked material layers 202 and 242 with the sheet 232 of pressure sensitive elastomer adhesive fibers may be accomplished by pressure bonding techniques such as, for example, pressure nip rollers or tensioned wind-up methods.

Additionally, the elastic sheet 232 may be a composite material in that it may be made of two or more individual coherent webs or it may be made of one or more webs individually containing a mixture of elastic and nonelastic fibers. An example of the latter type of elastic web is described in previously referenced U.S. Pat. No. 4,209,563. Another example of such a composite web would be one made by a technique such as disclosed in previously referenced U.S. Pat. No. 4,100,324.

Conventional drive means and other conventional devices which may be utilized in conjunction with the apparatus of FIG. 8 are well known and, for purposes of clarity, have not been illustrated in the schematic view of FIG. 8

EXAMPLES 1-4

The composite elastic materials of examples 1-4 were made by joining an elastic sheet to at least one reversibly necked material. The reversibly necked material was formed by tensioning a neckable material so that it constricted. The tensioned, necked material was heated and then cooled to ambient temperature while maintained in the necked condition. Reversibly necked material made in this manner was stretched to about its original, pre-necked dimensions and was found to return to generally its reversibly necked dimensions upon release of the stretching force. Tables 1-10 provide Grab Tensile Test data for control samples, reversibly necked material samples and composite elastic material samples.

The grab tensile tests were performed on a Constant Rate of

Extension tester, Instron Model 1122 Universal Testing Instrument using 4 inch by 6 inch samples. The following mechanical properties were determined for each sample: Peak Load, Peak Total Energy Absorbed, and Percent Elongation.

Control samples and treated samples were then cycled on the Instron Model 1122 with Microcon II—50 kg load cell. The jaw faces of the tester were 1 inch by 3 inches and the samples were cut to 3 inches by 7 inches (7 inches in the direction to be tested) and weighed individually in grams. A 4 inch gauge length was used. Chart and crosshead speeds were set for 20 inches per minute and the unit was zeroed, balanced and calibrated according to the standard procedure. The maximum extension limit for the cycle length was set at a distance determined by calculating 56 percent of the "elongation to break" from the Grab Tensile Test above. The sample was cycled to the specified cycle length four times and then was taken to break on the fifth cycle. The test equipment was set to report Peak Load in pounds force, Peak Elongation in percent and Peak Energy Absorbed in inch pounds force per square inch. The area used in the energy measurements (i.e., the surface area of material tested) is the gauge length (4 inches) times the sample width (3 inches) which equals twelve square inches. The results of the Grab Tensile Tests and cycle tests have been normalized for measured basis weight.

Peak Total Energy Absorbed (TEA) as used herein is defined as the total energy under a stress versus strain (load versus elongation) curve up to the point of "peak" or maximum load. TEA is expressed in units of work/(length)$^2$ or (pounds force * inch)/(inches)$^2$. These values have been normalized by dividing by the basis weight of the sample in ounces per square yard (osy) which produces units of [(lbs$_f$ * inch)/inch$^2$]/osy.

Peak Load as used herein is defined as the maximum amount of load or force encountered in elongating the sample to break. Peak Load is expressed in units of force (lbs$_f$) which have been normalized for the basis weight of the material resulting in a number expressed in units of lbs$_f$/(osy).

Elongation as used herein is defined as relative increase in length of a specimen during the tensile test. Elongation is expressed as a percentage, i.e., [(increase in length)/(original length)] × 100.

Permanent Set after a stretching cycle as used herein is defined as a ratio of the increase in length of the sample after a cycle divided by the maximum stretch during cycling. Permanent Set is expressed as a percentage, i.e., [(final sample length—initial sample length)/(maximum stretch during cycling—initial sample length)] × 100. Permanent Set is related to recovery by the expression [permanent set = 100 − recovery] when recovery is expressed as a percentage.

EXAMPLE 1

Neckable Spunbond Material

A neckable web of spunbond polypropylene having a basis weight of about 0.8 osy was tested on an Instron Model 1122 Universal Testing Instrument. The results are reported in Tables 1 and 2 under the heading "Control." The machine direction total energy absorbed is given in the column of Table 1 entitled "MD TEA." The machine direction peak load is given in the column entitled "MD Peak Load." The machine direction elongation to break is given in the column entitled "MD Elong." The cross-machine direction total energy absorbed is given in the column entitled "CD TEA." The cross-machine direction peak load is given in the column entitled "CD Peak Load." The cross-machine direction elongation to break is given in the column entitled "CD Elong."

The Peak TEA, Peak Load, and Permanent Set is given for each stretch cycle in Table 2. At the end of the series of cycles, the sample was elongated to break and the results reported under the heading "To Break." The value in the "Perm Set" row and "To Break" column is the break elongation measured during the final stretching.

Reversibly Necked Spunbond Material

A roll of the neckable spunbond polypropylene material having a basis weight of 0.8 osy and an initial width of about 17.75 inches was unwound on a "22 inch Face Coating Line rewinder" made by the Black-Clawson Company. The wind-up speed was set at about 4 to about 5 feet per minute and the unwind resistance force was set at 46 pounds per square inch causing the material to neck or constrict to a width of about 9 inches as the material was rewound on a roll. The roll of necked material was heated in a Fischer Econotemp ™ Lab Oven Model 30F at 120° C. for 6 hours which was thought to be more than the amount of time required to heat the entire roll, i.e., the center of the roll, to the oven temperature for about 300 seconds.

The reversibly necked material formed in this manner was tested on the Instron Model 1122 Universal Testing Instrument and the results are reported in Tables 1 and 2 under the heading "Heat Set." Necking and heat setting the spunbonded material decreased most tensile properties but increased cross-machine direction stretch.

Elastic Sheet

A blend of about 63% by weight KRATON G-1657, 20% polyethylene NA-601 and 17% REGALREZ 1126 having a melt flow of about 15 grams per ten minutes when measured at 190° C. and under a 2160 gram load; an elongation of about 750%; a modulus of elongation at 100% of about 175 psi; and a modulus of elongation at 300% of about 225 psi, was formed into an elastic sheet of meltblown fibers utilizing recessed die tip meltblowing process equipment having a 0.090 inch recess and a 0.067 inch air gap. The equipment was operated under the following conditions: die zone temperature about 540° F.; die polymer melt temperature about 535° F.; barrel pressure 580 psig; die pressure 190 psig; polymer throughput 2 pounds per hour; forming drum vacuum about 2 inches of water; horizontal forming distance about 12 inches; vertical forming distance about 12 inches and winder speed about 19 feet per minute.

The nonwoven web of meltblown elastic fibers had a basis weight of about 105 grams per square meter and a width of about 20 inches. The sheet was tested on the Instron Model 1122 Universal Testing Instrument and the results are given in Tables 1 and 2 under the heading "Elastomer 1."

In Table 2, Data collected in the last cycle (i.e. "to Break column") for the elastic sheet was read at the break elongation or peak value for the composite elastic material, i.e., 86% elongation so a direct comparison can be made between the composite and the elastomeric materials.

Composite Elastic Material

The reversibly necked material and the elastic sheet were joined using a Carver Laboratory Press Model 2518. Two 12 inch by 12 inch platens contacted the materials to be joined. The bottom platen was engraved with the sinusoidal dot pattern shown in FIG. 9. The bond pattern of the engraved plate has approximately 75 pins or bond points per square inch. Each pin has a diameter of about 0.059 inch to produce bond area of about 20.5 percent. The elastic sheet and the reversibly necked material were overlaid and placed between the press platens. The platens were heated to 100° F. and closed at a ram pressure of 15,000 psi and the overlaid materials were held in the press for 60 seconds to form a composite elastic material.

The composite elastic material was tested on the Instron Model 1122 Universal Testing Instrument and the results are given in Tables 1 and 2 under the heading "Composite 1". Properties of the reversibly necked material and the composite elastic material are shown in Table 3 under the respective headings of "Heat Set 1" and "Composite 1". It can been seen from Tables 1–3 that the reversibly necked material appears to act as a "positive stop" for the elastomer, as the "peak load" for composite 1 in Table 2 during the last cycle was almost five times the peak load for the elastomer at the same elongation. The elastic sheet lowers the normalized grab tensile strength data of the composite elastic material because the elastic sheet adds weight but little strength, especially in the machine direction, since the reversibly necked material has a low elongation to break in that direction. Permanent set is significantly lower in the composite elastic material than in the reversibly necked material.

EXAMPLE 2

The reversibly necked material and the elastic sheet of Example 1 were joined using a Carver Laboratory Press Model 2518 according to the procedure of Example 1. Two 12 inch by 12 inch platens contacted the materials to be joined. Both platens were smooth or flat so that the bond area would approach 100 percent. The elastic sheet and the reversibly necked material were overlaid and placed between the press platens. The platens were heated to 100° F. and closed at a ram pressure of 15,000 psi and the overlaid materials were held in the press for 60 seconds to form a composite elastic material with a bond area that approached 100 percent.

The composite elastic material was tested on the Instron Model 1122 Universal Testing Instrument and the results are given in Tables 4 and 5 under the heading "Composite 2. Tables 6 and 7 give the tensile test properties of both elastic composites. As discussed in Example 1, the results show that the reversibly necked material acts as a positive stop. Data collected during the last cycle (i.e., "to Break") for the elastic sheet was read at the break elongation or peak value for the composite elastic material.

EXAMPLE 3

Neckable Spunbond Material

A neckable web of spunbond polypropylene having a basis weight of about 0.4 osy Was tested on an Instron Model 1122 Universal Testing Instrument. The results are reported in Table 8 under the heading "Control 3."

Reversibly Necked Spunbond Material

A roll of the neckable spunbond polypropylene material having a basis weight of 0.4 osy and an initial width of 32 inches was necked on a "Camachine #10" Model 152755 rewinder made by the Cameron Machine Company, Brookland, N.Y. The winder was operated faster than the unwind to neck the material to a width of 20.5 inches. The necked material was then rewound on a "22 inch Face Coating Line rewinder" made by the Black-Clawson Company. The unwind speed was set at about 6.5 feet per minute and the wind-up speed was set at about 7.5 feet per minute causing the material to neck or constrict further to a width of about 13.5 to about 14 inches as it was rewound on a roll. The roll of necked material was heated in a Fischer Econotemp ™ Lab Oven Model 30F at 120° C. for 3.5 hours.

The reversibly necked material formed in this manner was tested on the Instron Model 1122 Universal Testing Instrument and the results are reported in Tables 8 and 9 under the heading "Heat Set". Necking and heat setting the spunbonded material decreased most tensile properties but increased cross-machine direction stretch.

Composite Elastic Material

The reversibly necked 0.4 osy spunbond polypropylene was fed onto the forming wire of a recessed die tip meltblowing machine having a 0.090 inch recess and a 0.067 inch air gap. A blend of about 63% by weight KRATON G-1657, 20% polyethylene NA-601 and about 17 REGALREZ having a melt flow of about 15 grams per ten minutes when measured at 190° C. and under a 2160 gram load; an elongation of about 750%; a modulus of elongation at 100% of about 175 psi; and a modulus of elongation at 300% of about 225 psi, was formed into an elastic web of meltblown fibers utilizing recessed die tip meltblowing process equipment having a 0.090 inch recess and a 0.067 inch air gap. The meltblowing process equipment operated under the following conditions: die zone temperature about 520° F.; die polymer melt temperature about 543° F.; barrel pressure 490 psig; die pressure 206 psig; polymer throughput 2.1 pounds per hour; horizontal forming distance about 12 inches; vertical forming distance about 14 inches and winder speed about 35 feet per minute.

Figure 9:
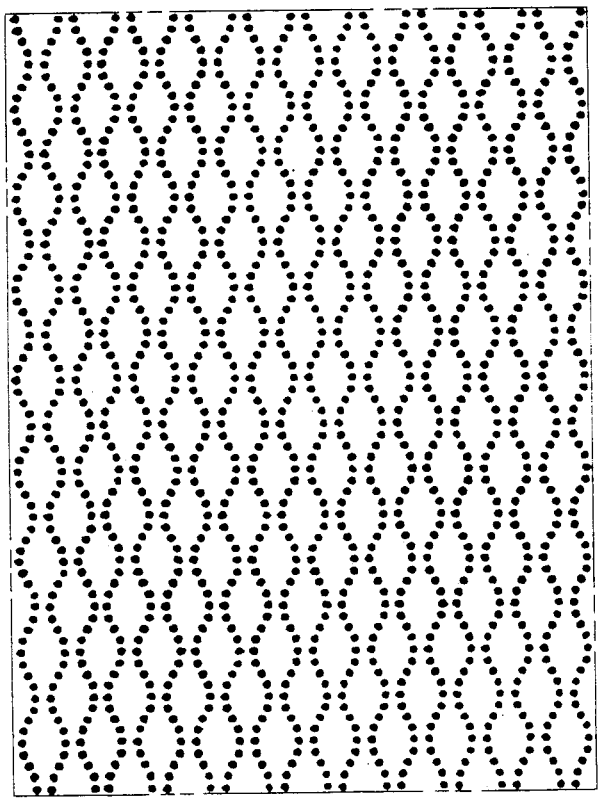
FIG. 9 is a representation of an exemplary bonding pattern used to join components of a composite elastic material.

The meltblown web of elastic fibers was formed directly on the reversibly necked material and had a basis weight of about 55 grams per square meter. The layers of elastic sheet and reversibly necked material were then joined with another layer of the same reversibly necked material utilizing a bonder roller arrangement having rollers running at about 15 feet per minute, a roller temperature of about 125° F., and a calender nip pressure of about 55 psi. The bond pattern utilized is shown in FIG. 9.

The spunbond/elastic/spunbond composite elastic material produced in this manner was tested on the Instron Model 1122 Universal Testing Instrument and the results are given in Tables 8 and 9 under the heading "Composite 3". Grab Tensile Test results were not significantly affected by the addition of an elastic sheet to the reversibly necked material. Cycling tensile results and permanent set were significantly improved.

EXAMPLE 4

Composite Elastic Material

A roll of the neckable spunbond polypropylene material described in Example 1 having a basis weight of 0.8 osy and an initial width of about 17.75 inches was unwound on a "22 inch Face Coating Line rewinder" made by the Black-Clawson Company. The wind-up speed was set at about 4 to about 5 feet per minute and the unwind resistance force was set at 48 pounds per square inch causing the material to neck or constrict to a width of about 8.5 to about 8.75 inches as it was rewound on a roll.

At the wind-up roll, a sheet of meltblown KRATON G fibers described in Example 1 having a basis weight of about 105 grams per square meter, was overlaid on the tensioned, necked material so that the two webs wound together on the wind up roll. The elastomeric web had a thin plastic film on one surface so it would stick to only one adjacent tensioned, necked material.

The tightly wound roll was heated in a Fischer Econotemp ™ Lab Oven Model 30F at 120° C. for 1 hour which was thought to be more than the amount of time required to heat the entire roll, i.e., the center of the roll, to the oven temperature for about 300 seconds. The material was cooled to ambient temperature completing the heat treatment of the tensioned, necked material to form a reversibly necked material. The heat treatment also softened the elastic sheet to improve bonding between the sheet and the reversibly necked material of the composite elastic material. The composite elastic material was tested on the Instron Model 1122 Universal Testing Instrument. The test results are reported in Tables 10 and 11 under the heading "Composite 4."

RELATED APPLICATIONS

This application is one of a group of commonly assigned patent applications which are being filed on the same date. The group includes application Ser. No. 07/249,050 in the name of Michael T. Morman and entitled; and application Ser. No. 07/248,548 also in the name of Michael T. Morman, entitled "Elastomeric Neck-Bonded Laminate". The subject matter of these applications is hereby incorporated herein by reference.

Disclosure of the presently preferred embodiment of the invention is intended to illustrate and not to limit the invention. It is understood that those of skill in the art should be capable of making numerous modifications without departing from the true spirit and scope of the invention.

TABLE 1

| GRAB TENSILES: | | |
|---|---|---|
| | Control 1 | Heat Set 1 |
| MD TEA | 1.05 ± .11 | .25 ± .06 |
| MD Peak Load | 15.8 ± 1.25 | 10.6 ± 1.0 |
| MD Elong | 46 ± 2 | 16 ± 2 |
| CD TEA | .89 ± .22 | .28 ± .05 |
| CD Peak Load | 13.2 ± 1.9 | 3.7 ± .5 |
| CD Elong | 50 ± 7 | 143 ± 6 |
| | Elastomer 1 | Composite 1 |
| MD TEA | 1.22 ± .13 | .085 ± .02 |
| MD Peak Load | 1.36 ± .09 | 3.23 ± .4 |
| MD Elong | 581 ± 39 | 18 ± 2 |
| CD TEA | .84 ± .22 | .24 ± .07 |
| CD Peak Load | .93 ± .12 | 1.63 ± .15 |
| CD Elong | 574 ± 95 | 147 ± 15 |

TABLE 2

| CYCLE: | 1 | 2 | 3 | 4 | To Break |
|---|---|---|---|---|---|
| Control 1, Cycled in Cross-Machine direction at 38% CD elongation | | | | | |
| Peak TEA | .932 ± .02 | .28 ± .01 | .24 ± .01 | .21 ± .01 | .50 ± .26 |
| Peak Load | 13.8 ± .2 | 11.8 ± .3 | 11.0 ± .1 | 10.4 ± .3 | 13.8 ± 1.7 |
| Perm. Set | 45 ± 3 | 49 ± 2 | 53 ± 1 | 55 ± 1 | 45 ± 4 |
| Heat Set 1, Cycled in Cross-Machine direction at 81% CD elongation | | | | | |
| Peak TEA | .033 ± .006 | .020 ± .003 | .018 ± .003 | .017 ± .002 | .41 ± .08 |
| Peak Load | .325 ± .07 | .30 ± .07 | .29 ± .06 | .28 ± .06 | 4.51 ± .6 |
| Perm. Set | 26 ± 1 | 30 ± 1 | 32 ± 2 | 42 ± 1 | 138 ± 6 |
| Elastomer 1, Cycled in Cross-Machine direction at 86% CD elongation | | | | | |
| Peak TEA | .049 ± .002 | .037 ± .001 | .036 ± .001 | .035 ± .001 | .089 ± .003 |
| Peak Load | .29 ± .01 | .28 ± .01 | .27 ± .01 | .27 ± .01 | .38 ± .01 |
| Perm. Set | 8 ± 0 | 9 ± 0 | 9 ± .4 | 10 ± .4 | — |
| Composite 1, Cycled in Cross-Machine direction at 86% CD elongation | | | | | |
| Peak TEA | .10 ± .02 | 0.6 ± .01 | .06 ± .01 | .056 ± .01 | .266 ± .03 |
| Peak Load | .73 ± .08 | .66 ± .07 | .64 ± .07 | .62 ± .07 | 1.88 ± .14 |
| Perm. Set | 10 ± 1 | 11 ± 1 | 12 ± 1 | 14 ± 2 | 135 ± 2 |

TABLE 3

| GRAB TENSILES: | | |
|---|---|---|
| | Heat Set 1 | Composite 1 |
| MD TEA | .25 ± .06 | .085 ± .02 |
| MD Peak Load | 10.6 ± 1.0 | 3.23 ± .4 |
| MD Elong | 16 ± 2 | 18 ± 2 |
| CD TEA | .28 ± .05 | .24 ± .07 |
| CD Peak Load | 3.7 ± .5 | 1.63 ± .15 |
| CD Elong | 143 ± 6 | 147 ± 15 |

TABLE 4

| GRAB TENSILES: | | |
|---|---|---|
| | Control 1 | Heat Set 1 |
| MD TEA | 1.05 ± .11 | .25 ± .06 |
| MD Peak Load | 15.8 ± 1.25 | 10.6 ± 1.0 |
| MD Elong | 46 ± 2 | 16 ± 2 |
| CD TEA | .89 ± .22 | .28 ± .05 |
| CD Peak Load | 13.2 ± 1.9 | 3.7 ± .5 |
| CD Elong | 50 ± 7 | 143 ± 6 |
| | Elastomer 1 | Composite 2 |
| MD TEA | 1.22 ± .13 | .11 ± .02 |
| MD Peak Load | 1.36 ± .09 | 3.7 ± .28 |
| MD Elong | 581 ± 39 | 19 ± 2 |
| CD TEA | .84 ± .22 | .28 ± .03 |
| CD Peak Load | .93 ± .12 | 1.8 ± .08 |

TABLE 4-continued

| GRAB TENSILES: | | |
|---|---|---|
| CD Elong | 574 ± 95 | 138 ± 13 |

TABLE 5

Control Cycled in the cross-machine direction at 38% CD elongation

| CYCLE: | 1 | 2 | 3 | 4 | To Break |
|---|---|---|---|---|---|
| *Control 1* | | | | | |
| Peak TEA | .932 ± .02 | .28 ± .01 | .24 ± .01 | .21 ± .01 | .50 ± .26 |
| Peak Load | 13.8 ± .2 | 11.8 ± .3 | 11.0 ± .1 | 10.4 ± .3 | 13.8 ± 1.7 |
| Perm. Set | 45 ± 3 | 49 ± 2 | 53 ± 1 | 55 ± 1 | 45 ± 4 |
| *Heat Set 1, Cycled in the cross-machine direction at 81% CD elongation* | | | | | |
| Peak TEA | .033 ± .006 | .020 ± .003 | .018 ± .003 | .017 ± .002 | .41 ± .08 |
| Peak Load | .325 ± .07 | .30 ± .07 | .29 ± .06 | .28 ± .06 | 4.51 ± .6 |
| Perm. Set | 26 ± 1 | 30 ± 1 | 32 ± 2 | 42 ± 1 | 138 ± 6 |
| *Elastomer 2, Cycled in the cross-machine direction at 86% CD elongation* | | | | | |
| Peak TEA | .049 ± .002 | .037 ± .001 | .036 ± .001 | .035 ± .001 | .089 ± .003 |
| Peak Load | .292 ± .007 | .28 ± .006 | .27 ± .006 | .27 ± .006 | .38 ± .01 |
| Perm. Set | 8 ± 0 | 9 ± 0 | 9.2 ± .5 | 10 ± .5 | — |
| *Composite 2, Cycled in the cross-machine direction at 86% CD elongation* | | | | | |
| Peak TEA | .169 ± .016 | .084 ± .009 | .077 ± .008 | .073 ± .008 | .329 ± .04 |
| Peak Load | .90 ± .09 | .80 ± .08 | .76 ± .08 | .74 ± .07 | 1.95 ± .13 |
| Perm. Set | 11 ± .4 | 13 ± .6 | 13.5 ± .5 | 15 ± .5 | 146 ± 8 |

TABLE 6

| GRAB TENSILES: | | |
|---|---|---|
| | Composite 1 | Composite 2 |
| MD TEA | .085 ± .02 | .11 ± .02 |
| MD Peak Load | 3.23 ± .4 | 3.7 ± .28 |
| MD Elong | 18 ± 2 | 19 ± 2 |
| CD TEA | .24 ± .07 | .28 ± .03 |
| CD Peak Load | 1.63 ± .15 | 1.8 ± .08 |
| CD Elong | 147 ± 15 | 138 ± 13 |

TABLE 7

| CYCLE: | 1 | 2 | 3 | 4 | To Break |
|---|---|---|---|---|---|
| *Composite 1, Cycled in the cross-machine direction at 86% CD elongation* | | | | | |
| Peak TEA | .10 ± .02 | .06 ± .01 | .06 ± .01 | .056 ± .01 | .266 ± .03 |
| Peak Load | .73 ± .08 | .66 ± .07 | .64 ± .07 | .62 ± .07 | 1.88 ± .14 |
| Perm. Set | 10 ± 1 | 11 ± 1 | 12 ± 1 | 14 ± 2 | 135 ± 2 |
| *Composite 2, Cycled in the cross-machine direction at 89% CD elongation* | | | | | |
| Peak TEA | .169 ± .016 | .084 ± .009 | .077 ± .008 | .073 ± .008 | .329 ± .04 |
| Peak Load | .90 ± .04 | .80 ± .08 | .76 ± .08 | .74 ± .07 | 1.95 ± .13 |
| Perm. Set | 11 ± .40 | 13 ± .6 | 13.5 ± .5 | 15 ± .5 | 146 ± 8 |

TABLE 8

| GRAB TENSILES: | | | |
|---|---|---|---|
| | Control 3 | Heat Set 3 | Composite 3 |
| MD TEA | .57 ± .18 | .17 ± .01 | .18 ± .02 |
| MD Peak Load | 13.8 ± 1.5 | 8.86 ± 1.0 | 6.1 ± .6 |
| MD Elong | 31 ± 5 | 14 ± 1 | 20 ± 1 |
| CD TEA | .69 ± .13 | .33 ± .05 | .36 ± .04 |
| CD Peak Load | 12.4 ± 2.3 | 4.26 ± .61 | 2.6 ± .3 |
| CD Elong | 42 ± 3 | 154 ± 6 | 182 ± 10 |

TABLE 9

| CYCLE: | 1 | 2 | 3 | 4 | To Break |
|---|---|---|---|---|---|
| *Heat Set 3, Cycled in the cross-machine direction at 90% CD elongation* | | | | | |
| Peak TEA | .016 ± .005 | .011 ± .003 | .010 ± .003 | .009 ± .002 | .451 ± .082 |
| Peak Load | .191 ± .065 | .174 ± .062 | .170 ± .06 | .168 ± .06 | 4.86 ± .86 |
| Perm. Set | 23 ± 1 | 26 ± 2 | 29 ± 2 | 45 ± 16 | 153 ± 9 |
| *Composite 3, Cycled in the cross-machine direction at 90% CD elongation* | | | | | |
| Peak TEA | .097 ± .009 | .046 ± .003 | .040 ± .003 | .037 ± .003 | .457 ± .06 |
| Peak Load | .63 ± .08 | .51 ± .06 | .47 ± .06 | .44 ± .06 | 2.96 ± .26 |
| Perm. Set | 13 ± 1 | 15 ± 1 | 16 ± 1 | 19 ± 1 | 172 ± 8 |

TABLE 10

| GRAB TENSILES: | |
|---|---|
| | Composite 4 |
| MD TEA | .25 ± .02 |
| MD Peak Load | 12.0 ± .3 |
| MD Elong | 16 ± 1 |
| CD TEA | .26 ± .06 |
| CD Peak Load | 3.7 ± .6 |
| CD Elong | 143 ± 10 |

TABLE 11

| CYCLE: | 1 | 2 | 3 | 4 | To Break |
|---|---|---|---|---|---|
| Composite 4, Cycled in the cross-machine direction at 80% CD elongation | | | | | |
| Peak TEA | .014 ± .001 | .004 ± .001 | .002 ± .001 | .002 ± .001 | .370 ± .121 |
| Peak Load | .213 ± .011 | .194 ± .008 | .185 ± .009 | .183 ± .009 | 4.06 ± .65 |
| Perm. Set | 22 ± 1 | 25 ± 1 | 28 ± 1 | 37 ± 3 | 143 ± 7 |
| Composite 4 Cycled in the machine direction at 9% MD elongation | | | | | |
| Peak TEA | .197 ± .02 | .137 ± .01 | .122 ± .02 | .113 ± .01 | .368 ± .07 |
| Peak Load | 16.3 ± .9 | 14.1 ± .6 | 13.4 ± .9 | 12.9 ± .6 | 19.8 ± 1.8 |
| Perm. Set | — | — | — | 16.2 ± 2 | 12 ± 8 |

What is claimed is:

1. A composite elastic material comprising at least one reversibly necked material joined to at least one elastic sheet at least at two locations.

2. The material of claim 1 wherein said reversibly necked material comprises a web selected from the group consisting of a bonded carded web of fibers, a web of spunbonded fibers, a web of meltblown fibers, and a multilayer material including at least one of said webs.

3. The material of claim 2 wherein said meltblown fibers include meltblown microfibers.

4. The material of claim 2 wherein said fibers comprise a polymer selected from the group consisting of polyolefins, polyesters, and polyamides.

5. The material of claim 4 wherein said polyolefin is selected from the group consisting of one or more of polyethylene, polypropylene, polybutene, ethylene copolymers, propylene copolymers, and butene copolymers.

6. The material of claim 2 wherein said reversibly necked material is a composite material comprising a mixture of fibers and one or more other materials selected from the group consisting of wood pulp, staple fibers, particulates and superabsorbents.

7. The material of claim 1 wherein said elastic sheet comprises an elastomeric polymer selected from the group consisting of elastic polyesters, elastic polyurethanes, elastic polyamides, and elastic A-B-A' block copolymers wherein A and A' are the same or different thermoplastic polymer, and wherein B is an elastomeric polymer block.

8. The material of claim 1 wherein said elastic sheet is an elastic web of meltblown fibers.

9. The material of claim 8 wherein said meltblown fibers include meltblown microfibers.

10. The material of claim 1 wherein said elastic sheet is a pressure sensitive elastomer adhesive sheet.

11. The material of claim 10 wherein the pressure sensitive elastomer adhesive sheet is formed from a blend of an elastomeric polymer and a tackifying resin.

12. The material of claim 11 wherein the blend further includes a polyolefin.

13. The material of claim 10 wherein said pressure sensitive elastomer adhesive sheet is a pressure sensitive elastomer adhesive web of meltblown fibers.

14. The material of claim 13 wherein said meltblown fibers include meltblown microfibers.

15. A composite elastic material comprising at least one reversibly necked polypropylene web joined to at least one elastic sheet at least at two locations.

16. The material of claim 15 wherein said reversibly necked polypropylene web is comprises a web selected from the group consisting of a bonded carded web of polypropylene fibers, a web of spunbonded polypropylene fibers, a web of meltblown polyproplyene fibers, and a multilayer material including at least one of said webs.

17. The material of claim 15 wherein said reversibly necked polypropylene web comprises a web formed from a mixture of fibers and one or more other materials selected from the group consisting of wood pulp, staple fibers, particulates and superabsorbents.

18. The material of claim 16 wherein said meltblown fibers include meltblown microfibers.

19. The material of claim 15 wherein said elastic sheet comprises an elastomeric polymer selected from the group consisting of elastic polyesters, elastic polyurethanes, elastic polyamides, and elastic A-B-A' block copolymers wherein A and A' are the same or different thermoplastic polymer, and wherein B is an elastomeric polymer block.

20. The material of claim 15 wherein said elastic sheet is an elastic web of meltblown fibers.

21. The material of claim 20 wherein said meltblown fibers include meltblown microfibers.

22. The material of claim 15 wherein said elastic sheet is a pressure sensitive elastomer adhesive sheet.

23. The material of claim 22 wherein said pressure sensitive elastomer adhesive sheet is formed from a blend of an elastomeric polymer and a tackifying resin.

24. The material of claim 23 wherein said blend further includes a polyolefin.

25. The material of claim 22 wherein said pressure sensitive elastomer adhesive sheet is a pressure sensitive elastomer adhesive web of meltblown fibers.

26. The material of claim 25 wherein said meltblown fibers include microfibers.

27. A method of producing a composite elastic material comprising joining at least one elastic sheet to at least one reversibly necked material at least at two places.

28. The method claim 27 wherein said reversibly necked material comprises a web selected from the group consisting of a bonded carded web of fibers, a web of spunbonded fibers, a web of meltblown fibers, and a multilayer material including at least one of said webs.

29. The method of claim 28 wherein said web of meltblown fibers include meltblown microfibers.

30. The method of claim 28 wherein said fibers comprise a polymer selected from the group consisting of polyolefins, polyesters, and polyamides.

31. The method of claim 30 wherein said polyolefin is selected from the group consisting of one or more of polyethylene, polypropylene, polybutene, ethylene copolymers, propylene copolymers, and butene copolymers.

32. The method of claim 27 wherein said reversibly necked material is a composite material comprising a mixture of fibers and one or more other materials selected from the group consisting of wood pulp, staple fibers, particulates and superabsorbent materials.

33. The method of claim 27 wherein said elastic sheet comprises an elastomeric polymer selected from the group consisting of elastic polyesters, elastic polyurethanes, elastic polyamides, and elastic A-B-A' block copolymers wherein A and A' are the same or different thermoplastic polymer, and wherein B is an elastomeric polymer block.

34. The method of claim 27 wherein said elastic sheet is an elastic web of meltblown fibers.

35. The method of claim 34 wherein said meltblown fibers include meltblown microfibers.

36. The method of claim 27 wherein said elastic sheet is a pressure sensitive elastomer adhesive sheet.

37. The method of claim 36 wherein said pressure sensitive elastomer adhesive sheet is formed from a blend of an elastomeric polymer and a tackifying resin.

38. The method of claim 37 wherein said blend further includes a polyolefin.

39. The method of claim 36 wherein said pressure sensitive elastomer adhesive sheet is a pressure sensitive elastomer adhesive web of meltblown fibers.

40. The method of claim 39 wherein said meltblown fibers include microfibers.

41. The method of claim 27 wherein said elastic sheet and said reversibly necked material are joined by forming said elastic sheet directly on said reversibly necked material.

42. The method of claim 36 wherein said pressure sensitive elastomer adhesive sheet and said reversibly necked material are joined by applying a tensioning force to said reversibly necked material and winding said reversibly necked material and said pressure sensitive elastomer adhesive sheet in a wind up roll so that pressure from said reversibly necked material activates the sheet and bonds the necked material to the pressure sensitive elastomer adhesive sheet.

* * * * *

UNITED STATES PATENT AND TRADEMARK OFFICE
CERTIFICATE OF CORRECTION

PATENT NO. : 4,981,747
DATED : January 1, 1991
INVENTOR(S) : Michael T. Morman

It is certified that error appears in the above-identified patent and that said Letters Patent is hereby corrected as shown below:

Column 2, line 18, "length final" should read --length - final--;

Column 4, line 10, "may by" should read --may be--;

Column 6, line 20, "maY" should read --may--;

Column 13, line 25, "02" should read --202--;

Column 13, line 53, "roller" should read --rollers--;

Column 14, line 29, "750%" should read --750%;--;

Column 14, line 35, "750%" should read --750%;--;

Column 14, line 38, "example" should read --example,--;

Column 17, line 35, "been" should read --be--

Column 18, line 8, "Was" should read --was--;

Column 19, line 68, "entitled;" should read --entitled "Reversibly Necked Material";--;

UNITED STATES PATENT AND TRADEMARK OFFICE
CERTIFICATE OF CORRECTION

PATENT NO. : 4,981,747

DATED : January 1, 1991

INVENTOR(S) : Michael T. Morman

It is certified that error appears in the above-identified patent and that said Letters Patent is hereby corrected as shown below:

Column 19, line 68, "07/248,548" should read --07/248,518--

Signed and Sealed this

Tenth Day of August, 1993

MICHAEL K. KIRK

Acting Commissioner of Patents and Trademarks